United States Patent
Botti et al.

(10) Patent No.: US 6,734,323 B2
(45) Date of Patent: May 11, 2004

(54) PROCESS FOR THE PREPARATION OF ZEOLITIC CATALYSTS

(75) Inventors: Giuseppe Botti, Milan (IT); Angela Carati, Milan (IT); Leonardo Dalloro, Milan (IT)

(73) Assignees: Enichem S.P.A., Milan (IT); Enitecnologie S.P.A., Milan (IT)

(*) Notice: Subject to any disclaimer, the term of this patent is extended or adjusted under 35 U.S.C. 154(b) by 0 days.

(21) Appl. No.: 09/725,292

(22) Filed: Nov. 29, 2000

(65) Prior Publication Data

US 2001/0002991 A1 Jun. 7, 2001

(30) Foreign Application Priority Data

Dec. 3, 1999 (IT) .......................... MI99A2538

(51) Int. Cl.⁷ ................................. B01J 29/06
(52) U.S. Cl. .......................... 564/123; 502/63; 502/64; 502/71
(58) Field of Search .................. 502/63, 64, 71; 423/713; 564/123

(56) References Cited

FOREIGN PATENT DOCUMENTS

| EP | 0 106 158 | 4/1984 |
|----|-----------|--------|
| EP | 0 265 018 | 4/1988 |
| EP | 0 906 784 | 4/1999 |

OTHER PUBLICATIONS

Derwent Abstracts, Accession No. 85–313590/50, JP60218307, Nov. 1, 1985.
Paul J. Kunkeler, et al. "Zeolite Beta: Characterization and passivation of the external surface acidity", Elsevier Science B.V., vol. 11, No. 5–6, Oct. 1997, pp. 313–323.
Guangyu Zhang, et al. "Preparation of Colloidal Suspensions of Discrete TS–1 Crystals", American Chemical Society, vol. 9, No. 1, Jan. 1, 1997, pp. 210–217.
J. Sudhakar Reddy, et al. "Synthesis, Characterization, and Catalytic Properties of a Titanium Silicate, TS–2, with MEL Structure", Journal Of Catalysis, US, Academic Press, vol. 130, No. 2, Aug. 1, 1991, pp. 440–446.
E. Jorda, et al. "TiF4: An Original and Very Interesting Precursor to the Synthesis of Titanium Containing Silicalite–1", Elsevier Science Publishing, vol. 19, No. 4, Oct. 1, 1997, pp. 238–245.

*Primary Examiner*—Tom Dunn
*Assistant Examiner*—Christina Ildebrando
(74) *Attorney, Agent, or Firm*—Oblon, Spivak, McClelland, Maier & Neustadt, P.C.

(57) ABSTRACT

The present invention relates to a process for the preparation of zeolitic catalysts comprising zeolite and oligomeric silica, which can be used in industrial reactors. The process consists in directly mixing the suspension, resulting from the synthesis of the zeolite, with an oligomeric silica sol, obtained from the hydrolysis of a tetra-alkyl ortho silicate in the presence of tetra-alkylammonium hydroxide, and in subjecting the mixture to rapid drying, by feeding to a spray-dry.

13 Claims, 4 Drawing Sheets

80 X 1

600 X

800 X

PROCESS FOR THE PREPARATION OF ZEOLITIC CATALYSTS

Figure 1A:
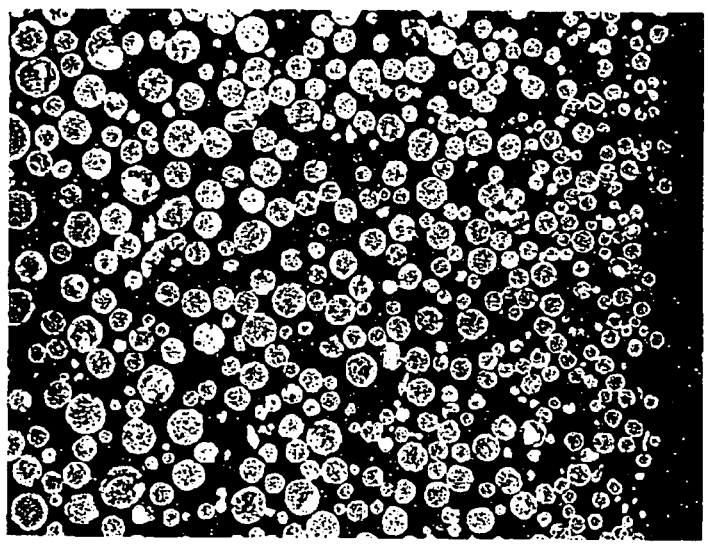

The present invention relates to a process for the preparation of zeolitic catalysts, comprising zeolite and oligomeric silica, which can be used in industrial reactors.

More specifically, the invention relates to a process for the preparation of zeolitic catalysts characterized by an original morphology which consists in directly mixing the suspension resulting from the synthesis of the zeolite with an oligomeric silica sol and in subjecting the mixture to rapid drying.

The invention also relates to the materials obtained by means of the above process and to the processes in which these are used as catalysts.

Zeolites and zeolitic materials are known in literature as basic components for the preparation of catalysts, which can be used in numerous reactions of industrial interest.

For example, zeolites of the MFI type with a low content of trivalent hetero-elements, are known in literature as base material for the preparation of catalysts which can be used in the transposition reaction of oximes to amides (EP 242, 960).

Zeolites of the MFI type, in which the hetero-element is Ti (Titanium-Silicalites TS-1) are known as materials for the preparation of catalysts which are used in many oxidation reactions, among which ammoximation reactions (U.S. Pat. Nos. 4,410,501; 4,794,198).

These materials however, if forming the only active component, have limited possibilities for use in industrial reactors.

In fact, whereas, on the one hand, the small dimensions of the zeolite crystals favour the intraparticle diffusion of the reagents and reaction products and allow good catalytic performances to be obtained, on the other hand similar dimensions can prevent interparticle diffusion in fixed bed reactors, or the separation of the zeolitic catalyst from the reaction medium in mixing reactors.

An increase in the dimensions, as also the resistance to friction and tensile strength, is generally obtained by combining the zeolitic material with compounds of an inorganic nature (ligands) in the forming phase.

The methods for the preparation of bound zeolites must be such as not to cause blockage of the zeolitic cavities, which would obviously create a reduction in the catalytic activity.

For reactions in which a catalytic contribution on the part of the ligand should be avoided, as for example in many oxidations and acid-catalyzed reactions, the use of a ligand of a catalytically inert material such as silica, is of particular interest.

Patent EP 265,018, for example, describes a process for preparing zeolitic catalysts based on the rapid drying of an aqueous dispersion consisting of crystalline zeolite, oligomeric silica and tetra-alkylammonium hydroxide.

The process, however, is complex and comprises a series of steps among which the separation of the zeolite crystals obtained from the hydro-thermal synthesis and their subsequent washing before dispersion in the aqueous solution of oligomeric silica previously formed by the hydrolysis of a tetra-alkyl ortho silicate in the presence of a tetra-alkylammonium hydroxide.

European patent application EP 906,784 discloses a simplified process for preparing catalysts comprising zeolites and oligomeric silica, which avoids the steps relating to the separation of the crystals and subsequent washing.

In practice, a tetra-alkyl ortho silicate compound is hydrolyzed directly in the suspension resulting from the synthesis of the zeolite, containing zeolite crystals and the residual templating agent (tetra-alkylammonium hydroxide).

The slurry obtained is then subjected to rapid drying by feeding to a spray-dry.

To avoid the separation step of the zeolite, a great advantage, from an industrial point of view, is mainly when operating with zeolite crystals having dimensions of less than 0.5 $\mu$m.

In this case, the crystals cannot be separated from the synthesis medium with the usual techniques, such as filtration or with continuous centrifugations, but require the use of more expensive techniques which operate batch-wise.

A new simplified process has now been found, which allows the preparation of zeolitic catalysts characterized by an original morphology and suitable for industrial use.

In particular, an object of the present invention relates to a process for the preparation of zeolitic catalysts based on the rapid drying of an aqueous dispersion comprising crystalline zeolite, oligomeric silica and tetra-alkylammonium hydroxide, characterized in that the aqueous dispersion is prepared by directly mixing the suspension resulting from the synthesis of the zeolite, with an oligomeric silica sol obtained from the hydrolysis of a tetra-alkyl ortho silicate compound in the presence of tetra-alkylammonium hydroxide.

The process according to the invention differs from that described in EP 906,784, in the preparation of oligomeric silica which, in this case, is obtained by separately hydrolyzing a tetra-alkyl ortho silicate compound in the presence of tetra-alkylammonium hydroxide, whereas in the process of the known art, the oligomeric silica precursor is added directly to the suspension resulting from the synthesis of the zeolite.

Figure 1B:
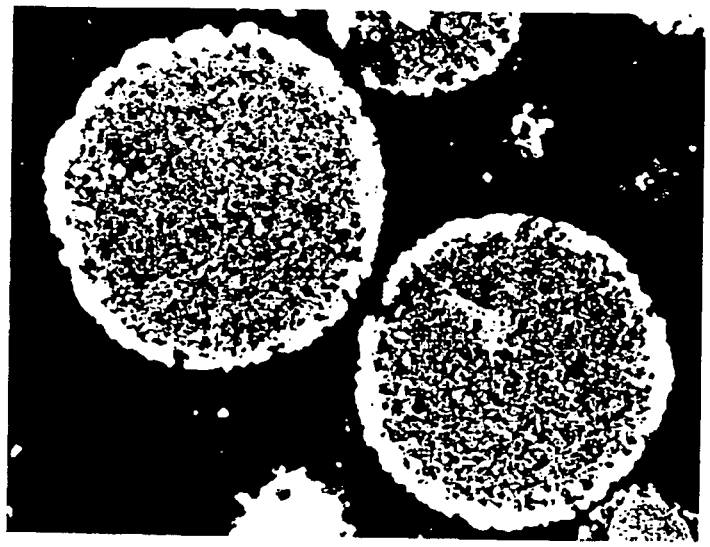
Figure 2:

Operating according to the process of the invention, catalysts are obtained in the form of microspheres having dimensions ranging from 5 to 300 $\mu$m, characterized by an external crown of essentially amorphous silica, which encloses inside an essentially crystalline low density phase consisting of zeolite (FIGS. 1, 2).

This particular morphology has never been described in the catalysts of the known art, in which the zeolite is generally uniformly dispersed in the amorphous silica chase.

The microspheres have a high crushing strength and a weight ratio oligomeric silica/zeolite ranging from 0.05 to 0.7.

The binding amorphous phase is characterized by an essentially mesoporous pore distribution and high surface area.

The process of the invention can be successfully applied to crystallization slurry of zeolites in which the molar ratio $H_2O/SiO_2$ is within the range of 4–35, whereas the molar ratio $H_2O/SiO_2$ of the zeolites prepared according to the process described in EP 906,784 ranges from 10 to 35, as lower ratios cause problems of instability of the slurry to be fed to the spray-dry.

The use of more concentrated reagent mixtures increases the productivity during the synthesis phase of the zeolite and creates more concentrated slurries in the feeding to the atomizer (a parameter which is known to significantly influence the dimensions of the atomized product).

Zeolites which are particularly suitable for being bound according to the present invention are those of the MFI, MFI/MEL and MEL group selected from:

1) MFI zeolites having the formula

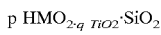
$$p\ HMO_{2-q}\ _{TiO2}\cdot SiO_2$$

wherein M is a metal selected from aluminum, gallium and iron, p has a value of 0 to 0.04 and q has a value ranging from 0.0005 to 0.03.

In particular when p is 0, the zeolite is Titanium-Silicalite TS-1 described in U.S. Pat. No. 4,410,501; zeolites in which p is different from 0 and M=Al, Ga and Fe are described in EP 226,257, EP 266,825 and EP 226,258, respectively;

2) MFI zeolites having the formula $$a\ Al_2O_3 \cdot (1-a)\ SiO_2$$

wherein a has a value ranging from 0 to 0.02.

In particular when a is 0 the zeolite is silicalite S-1 described in U.S. Pat. No. 4,061,724;

when a is different from 0 the zeolite is ZSM-5 described in U.S. Pat. No. 3,702,886 and in the new publication U.S. No. 29,948.

3) MEL or MFI/MEL zeolites having the formula $$x\ TiO_2 \cdot (1-x)\ SiO_2$$

wherein x has a value ranging from 0.0005 to 0.03.

These zeolites are described in BE 1,001,038 and are called TS-2 and TS-1/TS-2.

The binding phase consists of an amorphous mesoporous silica or silica-alumina synthesized as described in EP 340,868 and in EP 812,804.

It is therefore characterized by a high surface area and distributed pore volume in the mesoporous region.

This guarantees the absence of diffusion problems due to reactions typically catalyzed by zeolitic, i.e. microporous materials.

The active phase, which is enclosed in the crown of the amorphous ligand, fully preserves its specific characteristics, as its interactions with the binding phase are minimized.

The preparation of the zeolite according to the process of the invention takes place by the hydrothermal treatment at autogenous pressure, at a temperature ranging from 150 to 230° C. and for a time ranging from 0.5 to 48 hours, being the alkaline metals absent, of a mixture containing a silicon source, a tetra-alkylammonium hydroxide (TAA—OH), and optionally sources of Ti and/or Al, Ga, Fe.

The mixture has the following composition expressed as molar ratios:

Ti/Si=0–0.03;

M/Si=0–0.04 wherein M can be selected from Al, Ga or Fe;

TAA—OH/Si=0.2–0.5

$H_2O$/Si=4–35

The sources of silicon, titanium, aluminum, iron, gallium are those described in U.S. Pat. No. 4,410,501, EP 226,257, EP 266,825, EP 226,258.

The TAA—OH source is selected from those described in BE 1,001,038.

The binding phase of the process according to the present invention is prepared by mixing a silica source, optionally an aluminum source, a tetra-alkylammonium hydroxide, at a temperature ranging from 20° to 120° C. and for a time ranging from 0.2 to 24 hours.

The molar composition of the mixture is the following:

TAA—OH/$SiO_2$=0.04–0.40

$H_2O$/$SiO_2$=10–40

$Al_2O_3$/$SiO_2$=0–0.02

The sources of silica, aluminum, tetra-alkylammonium hydroxide are those described in EP 340,868 and in EP 812,804.

The alcohols present in the reagent mixture are those deriving from the hydrolysis of the reagents selected.

The $H_2O$/$SiO_2$ ratio=10–40 is selected so as to obtain a sol after the hydrolysis of the reagents.

The sol resulting from the preparation of the oligomeric silica is added to the crystallization slurry obtained from the preparation of the zeolite.

A plasticizing compound, such as for example, polyvinyl alcohol or methyl cellulose, can be optionally added in this phase.

The relative quantities of oligomeric silica sol and slurry, deriving from the crystallization of the zeolite, to be mixed together, are calculated so as to have a weight ratio oligomeric silica/zeolite ranging from 0.05 to 0.70.

The resulting slurry is treated under stirring at a temperature ranging from 25° C. to the boiling point of the mixture, for a period of time ranging from 1 to 48 hours. Preferably: 50–70° C., 1–6 hours.

The slurry, resulting from the mixing of the oligomeric silica with the zeolite, is subjected to rapid drying by means of spray-dry and the product obtained is calcined.

The atomization tests were carried out with Niro Mobile Minor HI-TEC spray, feeding with a 1.5 mm nozzle.

The form and dimensions of the catalysts produced are determined by means of SEM (Scanning Electron Microscopy) analysis on sections of samples.

The samples obtained can be used as catalysts, in particular for fluid bed applications.

When the zeolitic phase is silicalite-1 (MFI with only a silica composition), the catalyst formulated in accordance with the method object of the present invention can be successfully used in the catalytic transposition reaction of oximes to amides, such as the Beckmann catalytic transposition (transformation of cyclohexanone-oxime to ε-caprolactam).

In fact, the formulation method used allows the properties of the active phase to remain unaltered.

EXAMPLE 1

Synthesis of MFI Zeolite With a Molar Ratio $H_2O$/$SiO_2$=4

19.1 Kg of tetrapropylammonium hydroxide (TPA—OH) at 40% by weight in aqueous solution are charged into a 100 liter autoclave. 32.0 Kg of tetraethyl ortho silicate (TEOS) are added.

The temperature is brought to 190° C. and the mixture is left to crystallize at autogenous pressure for 2 hours.

The mixture is cooled to room temperature and a milky slurry is discharged from the reactor. 100 g of slurry are centrifuged obtaining 18 g of solid identified as pure MFI phase by means of XRD. The crystallization yield is 100%.

EXAMPLE 2

Synthesis of the Binding Phase 4.6 Kg of TPAOH at 40%, 24.2 Kg of water and 20.8 Kg of TEOS are charged in succession into a 100 liter autoclave. The mixture is heated to 60° C. for 1 hour to favour the hydrolysis. After cooling a limpid sol is discharged.

EXAMPLE 3

Formulation of the Catalyst (30% $SiO_2$–70% MFI)

15.0 Kg of slurry obtained as described in example 1 are mixed with 9.5 Kg of solution obtained as described in example 2. The mixture is heated to 70° C. for 3 h.

The slurry obtained is atomized with Niro Mobile Minor HI-TEC spray, feeding at a flow-rate of about 5 l/h with a 1.5 mm nozzle, with a temperature at the outlet of 100° C.

The product is discharged from the bottom of the chamber.

The morphology of the product determined by means of SEM analysis on the cut sample, is shown in FIG. 1a (magnification 80×), b(magnification 600×). The particular morphology of the spheres, consisting of a denser external crown which encloses inside a phase with a lower density, can be seen.

FIG. 2 illustrates the TEM image (Transmission Electron Microscopy) of a magnified section of the spheres (magnification 400,000×), showing a different composition between the external crown, essentially amorphous, and the center of the sphere, essentially crystalline, as demonstrated by the presence of lattice planes typical of the zeolitic phase.

Figure 3:
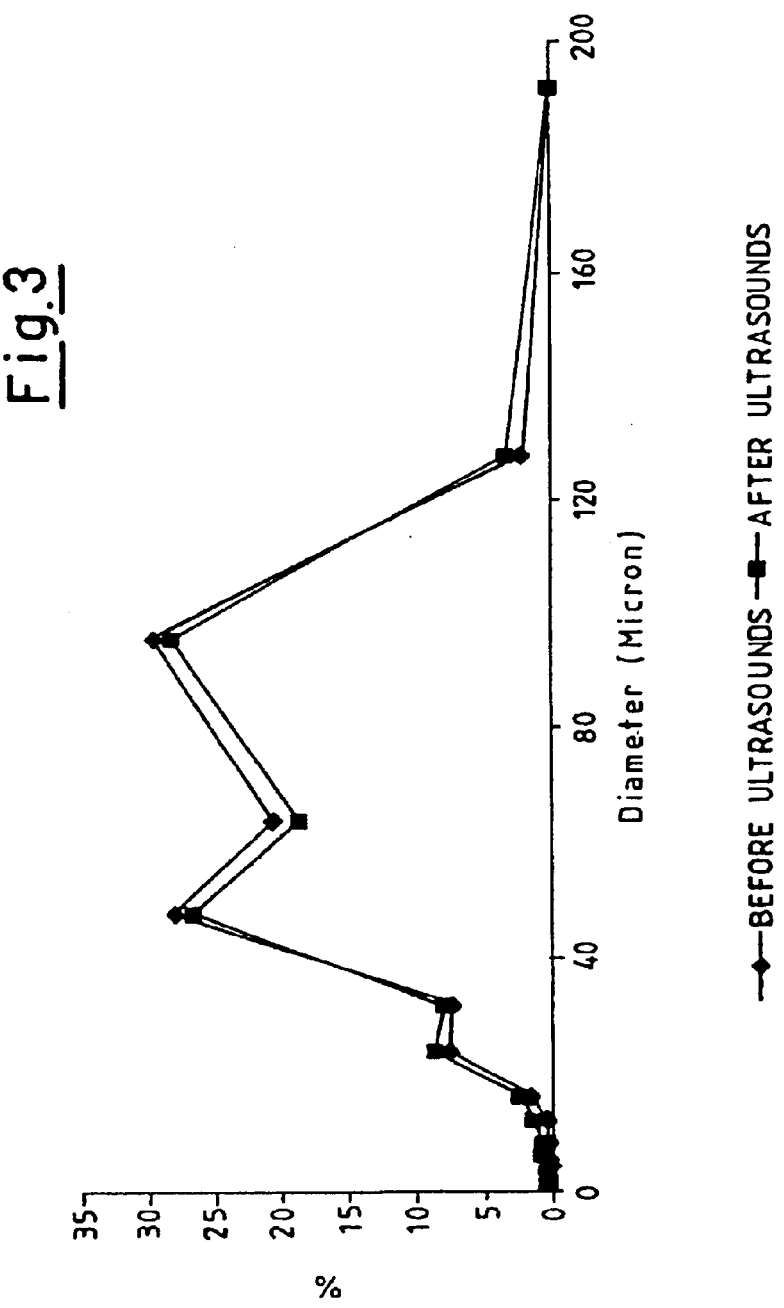

The average diameter, determined with a CILAS granulometer, is 47 μm. FIG. 3 indicates the particle size distribution curve of the sample before and after treatment of 1 hour in ultrasounds (Branson 5200 Bath). It can be observed that the distribution of the microspheres is not modified after the treatment; the catalyst therefore has a good crushing strength.

EXAMPLE 4

Synthesis of the Binding Phase 3.1 Kg of TPAOH at 40%, 34.1 Kg of water and 27.8 Kg of TEOS are charged in succession into a 100 liter autoclave. The mixture is heated to 60° C. for 1 hour to favour the hydrolysis. After cooling a limpid solution is discharged.

EXAMPLE 5

Formulation of the Catalyst (30% $SiO_2$–70% MFI)

15.0 Kg of slurry obtained as described in example 1 are mixed with 9.5 Kg of solution obtained as described in example 4 and 32 g of aqueous solution at 2% of polyvinyl alcohol. The mixture is heated to 70° C. for 3 h.

The slurry obtained is atomized with Niro Mobile Minor HI-TEC spray, feeding at a flow-rate of about 5 l/h with a 1.5 mm nozzle, with a temperature at the outlet of 100° C.

The product is discharged from the bottom of the chamber.

The average diameter determined with CILAS is 54 μm.

Figure 4:
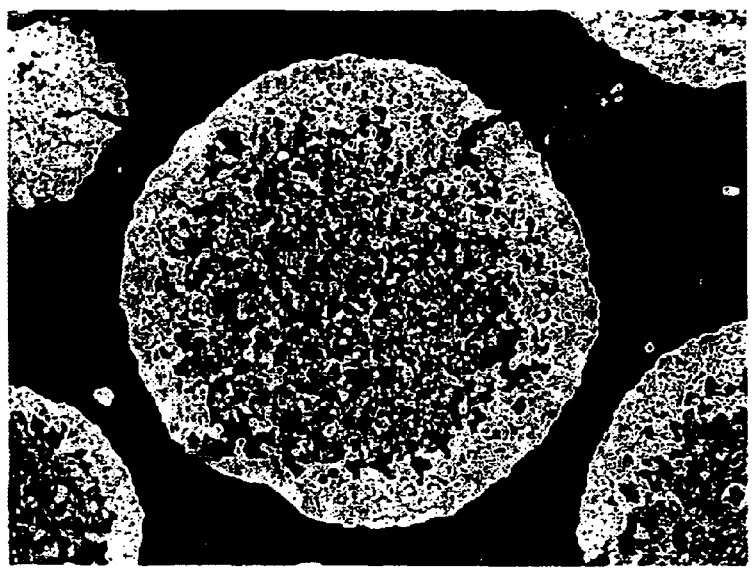

The morphology of the product determined by means of SEM analysis on the cut sample, is shown in FIG. 4 (magnification 800×).

EXAMPLE 6

Formulation of the Catalyst (50% $SiO_2$–50% MFI)

9.2 Kg of slurry obtained as described in example 1 are mixed with 13.9 Kg of solution obtained as described in example 4. The mixture is heated to 70° C. for 3 h.

The slurry obtained is atomized with Niro Mobile Minor HI-TEC spray, feeding at a flow-rate of about 3 l/h with a 1.5 mm nozzle, with a temperature at the outlet of 110° C.

The product is discharged from the bottom of the chamber.

The average diameter determined with CILAS is 62 μm.

EXAMPLE 7 (COMPARATIVE)

Synthesis of MFI Zeolite With a Molar Ratio $H_2O$/$SiO_2$=17

43.8 Kg of TPA—OH at 14% by weight in aqueous solution are charged into a 100 liter autoclave. 26.1 Kg of TEOS are added.

The temperature is brought to 190° C. and the mixture is left to crystallize at autogenous pressure for 2 hours.

The mixture is cooled to room temperature and a milky slurry is discharged from the reactor.

100 g of slurry are centrifuged obtaining 11 g of solid identified as pure MFI phase by means of XRD. The crystallization yield is 100%.

EXAMPLE 8 (COMPARATIVE)

Formulation of the Catalyst in Accordance With EP 906,784 (30% $SiO_2$–70% MFI)

22.0 Kg of slurry obtained as described in example 7 are mixed with 3.5 Kg of TEOS. The mixture is heated to 70° C. for 3 h.

The slurry obtained is atomized with Niro Mobile Minor HI-TEC spray, feeding at a flow-rate of about 5 l/h with a 1.5 mm nozzle, with a temperature at the outlet of 110° C.

The product is discharged from the bottom of the chamber.

The average diameter determined with CILAS is 43 μm.

Figure 5:
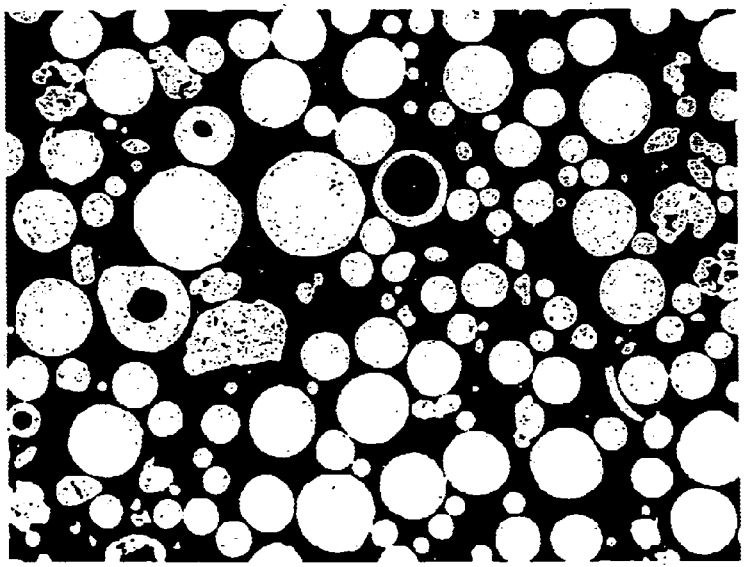

The morphology of the product determined by means of SEM analysis on the cut sample, is shown in FIG. 5 (magnification 160×).

No separation zones between the amorphous phase and crystalline phase are observed. The presence of both full compact spheres and spheres hollow inside, can be seen.

EXAMPLE 9 (COMPARATIVE)

5 Kg of slurry obtained as described in example 1 are mixed with 1.3 Kg of TEOS. The mixture is heated to 70° C. for 3 h. A heterogeneous mixture is obtained, which cannot be stirred and cannot therefore be fed to the spray-dry.

The type of preparation described in EP 906,784 can be applied to the crystallization slurry obtained with the synthesis described in example 1.

EXAMPLE 10

Catalytic Test

The catalyst prepared in example 5 is charged into a glass reactor (length 20 cm, internal diameter 1 cm) preheated to 350° C. in nitrogen and dried for 1 hour. A mixture of Methanol/Toluene with a molar ratio 1/1 is then sent onto the catalyst for 30 minutes. The catalytic test is subsequently started by feeding a mixture of Cyclohexanoneoxime/Methanol/Toluene/$N_2$ (molar ratio 1/10/10/8) preheated and vaporized (Weight Hourly Space Velocity referring to the cyclohexanone-oxime=4.5 $h^{-1}$). The temperature of the catalytic bed is maintained at 350° C. The mixture of effluent products from the reactor is condensed and analyzed by gaschromatography.

The conversion profiles (C %) and selectivity (S %) are indicated in FIG. 6.

What is claimed is:

1. A process for the preparation of a zeolitic catalyst comprising crystalline zeolite, oligomeric silica and tetra-alkyl ammonium hydroxide comprising:
   synthesizing a zeolite suspension,
   hydrolyzing a tetra-alkyl ortho silicate in the presence of a tetra-alkyl ammonium hydroxide to form an oligomeric silica sol,
   directly mixing the zeolite suspension with the oligomeric silica sol to form an aqueous dispersion, and spray drying the aqueous dispersion.

2. The process according to claim 1, wherein the zeolite is prepared by means of a hydrothermal treatment, at autogenous pressure, at a temperature ranging from 150 to 230° C. and for a time ranging from 0.5 to 48 hours, without alkaline metals, of a mixture comprising a silicon source, a tetra-alkyl ammonium hydroxide (TAA—OH), and optionally sources of Ti and/or Al, Ga, Fe.

3. The process according to claim 2, wherein the mixture subjected to hydrothermal treatment has the following composition expressed as molar ratios:

Ti/Si=0–0.03;

M/Si=0–0.04 wherein M can be selected from Al, Ga or Fe;

TAA—OH/Si=0.2–0.5;

$H_2O$/Si=4–35.

4. The process according to claim 1, wherein the oligomeric silica is prepared by means of the hydrolysis, at a temperature ranging from 20° to 120° C. and for a time ranging from 0.2 to 24 hours, of a mixture comprising a silica source, optionally an aluminum source and a tetra-alkylammonium hydroxide, having the following molar composition:

TAA—OH/$SiO_2$=0.04–0.40;

$H_2O$/$SiO_2$=10–40;

$Al_2O_3$/$SiO_2$=0–0.02.

5. The process according to claim 1, wherein the relative quantities of the oligomeric silica sol and of the zeolite suspension are calculated so as to have a weight ratio of oligomeric silica/zeolite ranging from 0.05 to 0.70.

6. The process according to claim 1, further comprising treating the aqueous dispersion comprising crystalline zeolite, oligomeric silica and tetra-alkyl ammonium hydroxide under stirring at a temperature ranging from 25° C. to the boiling point of the mixture, for a period of time ranging from 1 to 48 hours, and spray drying the aqueous dispersion to form microspheres and calcining the microspheres.

7. The process according to claim 6, further comprising treating the aqueous dispersion at a temperature ranging from 50 to 70° C. and for a period of time ranging from 1 to 6 hours.

8. The process according to claim 1, wherein the zeolites are selected from the group consisting of MFI, MEL, or MFI/MEL zeolites.

9. The process according to claim 1, wherein the zeolites are selected from the group consisting of:

MFI zeolites having the formula $$p\ HMO_2 \cdot q\ TiO_2 \cdot SiO_2,$$

wherein M is a metal selected from aluminum, gallium and iron, p has a value of 0 to 0.04 and q has a value ranging from 0.0005 to 0.03, MFI zeolites having the formula $$a\ Al_2O_3 \cdot (1-a)\ SiO_2,$$

wherein a has a value ranging from 0 to 0.02; and

MEL or MFI/MEL zeolites having the formula $$x\ TiO_2 \cdot (1-x)\ SiO_2,$$

wherein x has a value ranging from 0.0005 to 0.03.

10. The process according to claim 8, wherein the MFI zeolite is selected from the group consisting of Titanium-Silicalite TS-1, Silicalite S-1 and ZSM-5, and the MEL or MFI/MEL zeolite is selected from the group consisting of TS-2 and TS-1/TS-2 zeolite.

11. A zeolitic catalyst comprising microspheres having dimensions ranging from 5 to 300 μm comprising an external crown of substantially amorphous silica which encloses inside a substantially crystalline low density phase of zeolite, having a weight ratio of oligomeric silica/zeolite ranging from 0.05 to 0.7, obtained by the process according to claim 1.

12. Catalytic processes carried out in the presence of the catalysts according to claim 11.

13. A process for the preparation of amides from oximes carried out in the presence of a catalyst according to claim 11, wherein the zeolite is silicalite S-1.

* * * * *